(12) United States Patent
Hamamoto et al.

(10) Patent No.: US 7,655,687 B2
(45) Date of Patent: Feb. 2, 2010

(54) ANTI-INFLAMMATORY ANALGESIC FOR EXTERNAL USE

(75) Inventors: Hidetoshi Hamamoto, Itano-gun (JP); Masaki Ishibashi, Naruto (JP); Sueko Matsumura, Higashikagawa (JP); Keiko Yamasaki, Higashikagawa (JP)

(73) Assignee: Medrx Co., Ltd., Kagawa (JP)

( * ) Notice: Subject to any disclaimer, the term of this patent is extended or adjusted under 35 U.S.C. 154(b) by 472 days.

(21) Appl. No.: 10/587,862

(22) PCT Filed: Jan. 27, 2005

(86) PCT No.: PCT/JP2005/001540

§ 371 (c)(1),
(2), (4) Date: Jul. 28, 2006

(87) PCT Pub. No.: WO2005/072775

PCT Pub. Date: Aug. 11, 2005

(65) Prior Publication Data

US 2007/0054952 A1    Mar. 8, 2007

(30) Foreign Application Priority Data

Jan. 29, 2004    (JP) .............................. 2004-021232

(51) Int. Cl.
*A61K 31/407*    (2006.01)
*A61K 31/24*    (2006.01)
*A61P 29/00*    (2006.01)

(52) U.S. Cl. ...................... 514/411; 514/537

(58) Field of Classification Search ................. 514/411, 514/537
See application file for complete search history.

(56) References Cited

U.S. PATENT DOCUMENTS 5,958,445 A    9/1999    Humber et al.

7,018,647 B1    3/2006    Yamasaki et al.
7,166,641 B2 *    1/2007    Lee et al. .................... 514/561
2003/0129208 A1    7/2003    Alberts et al.
2007/0054952 A1    3/2007    Hamamoto et al.

FOREIGN PATENT DOCUMENTS

| EP | 1 716 868 | 11/2006 |
|---|---|---|
| JP | 64-040420 | 2/1989 |
| JP | 9-3071 | 1/1997 |
| JP | 2002-128699 | 5/2002 |
| JP | 2003-335663 | 11/2003 |
| JP | 2005-082512 | 3/2005 |
| JP | 2005-239709 | 9/2005 |
| WO | 01/47559 | 7/2001 |
| WO | 03/099293 | 12/2003 |

OTHER PUBLICATIONS

Supplementary Partial European Search Report issued May 18, 2009 in corresponding European Application No. 05 70 4361.
Reinhart et al., Postoperative Analgesia After Peripheral Nerve Block for Podiatric Surgery: Clinical Efficacy and Chemical Stability of Lidocaine Alone Versus Lidocaine Plus Ketorolac, XP-002252102, Regional Anesthesia and Pain Medicine, vol. 25, No. 5 (Sep.-Oct.), 2000, pp. 506-513.

* cited by examiner

*Primary Examiner*—Sreeni Padmanabhan
*Assistant Examiner*—Sahar Javanmard
(74) *Attorney, Agent, or Firm*—Wenderoth, Lind & Ponack, L.L.P.

(57) ABSTRACT

An objective of the present invention is to provide an anti-inflammatory analgesic for external use comprising etodolac as NSAID. The anti-inflammatory analgesic for external use is excellent not only in skin permeability but also in penetratability and diffusivity into tissues present in portions deeper than the skin, can act directly on the muscles or joint tissues with inflammation or pain, and is a little irritant to the skin. The anti-inflammatory analgesic for external use of the present invention is characterized by comprising etodolac and a local anesthetic.

2 Claims, No Drawings

ANTI-INFLAMMATORY ANALGESIC FOR EXTERNAL USE

TECHNICAL FIELD

The present invention relates to an external preparation having an anti-inflammatory analgesic effect.

BACKGROUND ART

Conventionally, a Non-Steroidal Anti-Inflammatory Drug (hereinafter, referred to as "NSAID") is known as an anti-inflammatory analgesic. This NSAID has an action of suppressing production of prostaglandin correlated with inflammation and pain, by inhibiting cyclooxygenase (hereinafter, referred to as "COX") catalyzing an initial step in an arachidonate cascade which is a metabolic route intensifying pain.

However, since prostaglandin has various actions in addition to actions such as inflammation and pain, serious side effects may occur in some cases in case that production of prostaglandin is suppressed to an extent more than necessary by administration of NSAID. For example, when the action of COX is suppressed, the activity of lipoxygenase is enhanced to increase leukotriene. As the result, secretion of gastric juice decreases, and simultaneously active oxygen disrupting a mucous membrane of a digestive tract increases, leading to the development of an ulcer. Additionally, side effects such as kidney function impairment, liver function impairment, skin eruption are known, and aspirin asthma may be induced particularly as a life-threatening side effect.

Accordingly, regarding NSAID, external preparations with a relatively low risk of these side effects have been developed. That is, such an external preparation delivers NSAID transdermally to an affected area so that systemic side effects can be reduced and the drug concentration can be enhanced in a local affected area.

However, some NSAIDs are extremely poor in skin permeability and their effects remarkably decrease in case that they are administered as external preparations compared with the case of oral administration. Then, technologies for improving skin permeability of NSAIDs are developed variously.

For example, an invention described in Kokai Publication No. Hei 14-128699 is an anti-inflammatory analgesic preparation for external use containing an NSAID and a local anesthetic, and has an object to be solved of improving skin permeability. In an example of this publication, a preparation containing loxoprofen sodium as an NSAID and a local anesthetic is prepared, and a test for evaluating its skin permeability is described.

However, evaluation of only skin permeability is not satisfactory for determining a value of a drug delivery system of an NSAID. The reason for this is that a portion generating pain is muscle tissue and joint tissue, and a portion to which an NSAID should reach is not a skin surface portion at which capillary blood vessels are present, but is a deeper portion at which muscle tissues and the like are present. Namely, when skin permeability and blood concentration are especially improved, the drug may not necessarily have an effect of penetratability and diffusivity in muscle tissues or the like and may not act directly on an affected area. Actually, according to findings of the present inventors, penetratability and diffusivity of some kind of NSAID in tissues are deteriorated by adding a local anesthetic. Nonetheless, in conventional preparation design, penetratability and diffusivity into portions deeper than corium are not taken into consideration at all under present circumstances.

Further, even with a preparation showing high skin permeability, unless it allows an NSAID to penetrate and diffuse into a deeper portion, the drug cannot but remain on a surface portion of the skin. As the result, secondary disorders such as decrease in safety due to skin irritation and the like are possibly caused. Additionally, it is thought that when the concentration of an NSAID inside the skin increases, concentration gradient against the drug present on the surface of the skin decreases, and therefore its absorption efficiency is deteriorated. Consequently, even if the content of an NSAID in an external preparation is increased, the amount to be absorbed does not increase and its effect is neither improved, thus, the NSAID concentration in traditional external preparations is at most about 1%, and its effect is recognized to be saturated even if it is further added.

Other preparations containing an NSAID and a local anesthetic are also known, like the invention described in Kokai Publication No. Hei 14-128699. For example, WO 01/047559 describes a patch drug for external use containing a local anesthetic and an NSAID, from the point of view of letting it act on both the inflammatory portion and the peripheral nervous system, and indomethacin and the like are exemplified as specific examples of NSAID. However, there is no description regarding etodolac nor skin permeability and the like, although this publication discloses the result of a sensory evaluation test as an example.

Also WO 03/099293 describes salts formed with an NSAID having a carboxyl group and a local anesthetic having an amino group, and describes etodolac as an example of NSAID. However, the technology described in this publication is directed to enhancing drug-sustained-releasability of an injection and the like by decreasing water-solubility of NSAID, but is not directed to external use. Thus, there are neither descriptions nor suggestions at all regarding skin permeability, nor penetratability nor diffusivity in muscle tissues and the like. Actually, produced salts in examples of this publication are only those containing diphnysal as an NSAID.

By the way, there are mainly type 1 and type 2 isozymes of COX. COX-1 is expressed constitutively in most tissues of the body, and is thought to fill the role of maintaining stability of the body including a stomach mucous membrane protecting action and the like. On the other hand, though the expression level of COX-2 under usual conditions is low, it is induced by inflammatory irritation and the like. Thus, it is thought that when COX-2 can be inhibited selectively, inflammation and the like can be reduced while suppressing the body damage. However, NSAIDs such as indomethacin, dichlofenac and the like, disclosed specifically as examples in the prior publications described above, inhibit COX non-selectively. That is, even if skin permeability of these external preparations is enhanced, side effects accompanying the increase of drug concentration in plasma can cause a problem, rendering the external preparations meaningless.

DISCLOSURE OF THE INVENTION

As describe above, preparations containing an NSAID and a local anesthetic have been known. Among external preparations containing loxoprofen, there exist those in which improvement of skin permeability is considered. However, in conventional technologies there is no consideration which is given to the penetratability and diffusivity in muscle and joint tissues under the skin. Further, according to findings of the present inventors, behavior of a preparation containing an NSAID and a local anesthetic is not uniform in muscle tissues, and owing to the co-existence of a local anesthetic, the penetratability and diffusivity of NSAID may be deteriorated by contraries in some cases.

Accordingly, a problem to be solved by the present invention is to provide an anti-inflammatory analgesic for external use containing an NSAID. The anti-inflammatory analgesic is excellent not only in skin permeability but also in penetratability and diffusivity into tissues present in portions deeper than the skin, capable of acting directly on the muscles or joint tissues with inflammation or pain, and a little irritant to the skin.

For solving the above-mentioned problem, the present inventors have intensively studied a preparation containing an NSAID, particularly, a constitution excellent in penetratability and diffusivity in muscle tissues and the like. As the result, the present inventors have found that a preparation, containing a local anesthetic together with etodolac which is an NSAID having a unique chemical structure, has remarkably higher penetratability and diffusivity in muscle tissues and the like as compared with other preparations of combination type, leading to completion of the present invention.

The anti-inflammatory analgesic for external use of the present invention is characterized by comprising etodolac and a local anesthetic.

In the above-mentioned anti-inflammatory analgesic for external use, it is preferable that the mass proportion of the local anesthetic based on 1 part by mass of the etodolac is 0.1 to 1.5 parts by mass. Likewise, it is preferable that the molar ratio of the local anesthetic to the etodolac is from 0.1 to 1.8. The reason for this range is that the object of the present invention can be attained within this range, and that the preparation excellent in skin permeability, and penetratability and diffusivity can be obtained.

As the above-mentioned local anesthetic, lidocaine is preferable. The reason for this is that the combination of lidocaine with etodolac is proved to be preferable in examples described later.

BEST MODES FOR CARRYING OUT THE INVENTION

The anti-inflammatory analgesic for external use of the present invention not only has an excellent skin permeability but also has remarkably improved penetratability and diffusivity into deep portions under the skin such as muscle tissues and the like. As the result, decrease of drug absorption is suppressed, thus, even if NSAID (etodolac) is added in a relatively large amount in a preparation, its effect can be brought to the fullest. Also the skin irritation which is problematical in conventional NSAID-containing external preparations is decreased. Therefore, the anti-inflammatory analgesic for external use of the present invention is extremely excellent as a preparation used for therapy and treatment of chronic rheumatoid arthritis, osteoarthritis, chronic pain such as lumbago; inflammatory diseases such as periarthritis scapulo-humeralis, tendovaginitis and the like; cervicobrachial syndrome; pains caused by surgery, injury and the like.

The anti-inflammatory analgesic for external use of the present invention is characterized by comprising etodolac and a local anesthetic.

Etodolac used in the present invention has a chemical name: 1,8-diethyl-1,3,4,9-tetrahydropyrano[3,4-B]indole-1-acetic acid, and has been used as an analgesic anti-inflammatory agent. In the present invention, those synthesized by a known method, or commercially available etodolac may be used.

Based on many common chemical structures of NSAIDs, NSAIDs can be classified into indole acetates typified by indomethacin, salicylates such as diphnysal and the like, phenylpropionates such as loxoprofen and the like, phenylacetates such as dichlofenac and the like, oxicumates such as meroxycum and the like. However, etodolac known as an excellent NSAID has a unique chemical structure as described below, and dose not belong to any of these categories.

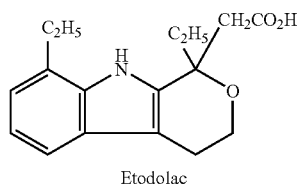

Etodolac

Further, etodolac is an excellent selective inhibitor of COX-2. Accordingly, although the external preparation of the present invention is excellent in skin permeability, the risk of side effects is low even if blood concentration increases when administered externally. Additionally, the external preparation of the present invention also has penetratability and diffusivity in muscle tissues and the like, thus, it does not happen that etodolac stagnates on the skin and only the blood concentration increases being absorbed from blood capillaries. Therefore, etodolac can be allowed to act locally.

"Local anesthetic" used in the present invention is not particularly restricted as long as it is used conventionally as a local anesthetic for medical use, and examples thereof include lidocaine, tetracaine, procaine, dibucaine, benzocaine, bupivacaine, mepivacaine, and salts thereof. One or more of them are preferably selected for use. Among these local anesthetics, lidocaine is particularly preferable. This is because the excellent effect of lidocaine is demonstrated in examples described later.

It is preferable that "local anesthetic" to be used should have a cation group such as an amino group and the like. This is because, through ionic association of such a cationic group and a carboxyl group of etodolac, the ionic group part is coated with a hydrophobic part to improve pharmacokinetics, thereby improving skin permeability, penetratability and diffusivity, and skin irritation.

The amount of etodolac compounded in the external preparation of the present invention is preferably 1 to 50 wt % in relation to the whole external preparation. When the compounding amount is less than 1 wt %, an analgesic effect may be insufficient in some cases, and when over 50 wt %, a side effect may be strengthened in some cases. In the external preparation of the present invention, the effect is not saturated and can be exerted depending on the compounding amount, since penetratability and diffusivity in muscle tissues and the like is improved together with skin permeability of etodolac. Therefore, the compounding amount of etodolac is more preferably 3 wt % or more, and particularly preferably 5% or more. Because of the same reason, the amount of a local anesthetic to be compounded in the external preparation of the present invention is also preferably 1 to 50 wt % in relation to the whole external preparation.

The compounding proportion of the etodolac and the local anesthetic in the external preparation of the present invention is not particularly restricted, but it is preferable that the proportion of the local anesthetic based on 1 part by mass of the etodolac is 0.1 to 1.5 parts by mass. Likewise, the molar ratio of both compounds is not particularly restricted, but it is preferable that they are compounded so that the molar ratio of the local anesthetic to the etodolac is from 0.1 to 1.8. This is because, within these ranges, skin permeability, and penetratability and diffusivity of etodolac can be improved. Further, it is more preferable that the above-mentioned compounding proportion is about 0.2 parts by mass or more and about 1.1 parts by mass or less, and the above-mentioned molar ratio is about 0.2 or more and about 1.3 or less. This is because, by rendering the number of moles of the etodolac and the number of moles of the local anesthetic approximately equal, considering the use as a medical product, a preparation excellent particularly in skin permeability, and penetratability and diffusivity can be obtained. Here, the above-mentioned ranges are used in a wide range since the object of the present invention can be achieved even if either drug is used in somewhat excess amount. For example, the effect of the present invention can be achieved sufficiently, when the amount of etodolac (molecular weight: 287.35) and the amount of lidocaine (molecular weight: 234.34) in a preparation are equal and the number of moles of lidocaine is somewhat larger than the molar number of etodolac, as shown in an example described later.

The dosage form of the external preparation of the present invention includes, for example, ointment, lotion, aerosol, plaster, aqueous pap, and the like, and the dosage form used for external use is not particularly restricted.

In the external preparation of the present invention, if necessary, the following component can be compounded in usual compounding amount: bases (e.g., rubbers such as natural rubber, isoprene rubber, polyisobutylene, styrene-isoprene-styrene block copolymer, styrene-butadiene-styrene block copolymer, styrene-ethylene•butylene-styrene block copolymer, alkyl ester of (meth)acrylate (co)polymer, poly(meth)acrylates, polyisobutylene, polybutene, liquid polyisoprene and the like; oils such as vaseline, cetanol, beeswax, lanolin, liquid paraffin and the like, water-soluble polymers such as carboxy vinyl polymer, acrylic acid starch, sodiumpolyacrylate, calmerose sodium, polyethylene glycol and the like; crotamiton; diethyl sebacate; anhydrous silicic acid and the like), excipients (e.g., saccharides such as sucrose and the like; starch derivatives such as dextrin and the like; cellulose derivatives such as carmellose sodium and the like; water-soluble polymers such as xanthan gum and the like), coloring agents, emulsifiers, thickening agents, wetting agents (e.g., glycerin and the like), stabilizers (e.g., p-hydroxybenzoates such as methylparaben, propylparaben and the like; alcohols such as chlorobutanol, benzyl alcohol, phenyl ethyl alcohol; benzalkonium chloride; phenols such as phenol, cresol and the like; thimerosal; acetic anhydride; sorbic acid and the like), preservatives, solvents (e.g., water, propylene glycol, butylenes glycol, isopropanol, ethanol, glycerin, diethyl sebacate, isopropyl myristate, diisopropyl adipate, myristyl palmitate, stearyl stearate, myristyl myristate, ceryl lignocerate, lacceryl cerotate, lacceryl lacerate and the like), solubilizing agents, suspending agents (e.g., carmellose sodium and the like), antioxidants (e.g., sodium hydrogen sulfite, L-ascorbic acid, sodium ascorbate, butylhydroxyanisole, butylhydroxytoluene, propyl gallate, tocopherol acetate, dl-α-tocopherol and the like), secondary ingredients (e.g., peppermint oil, L-menthol, camphor, thymol, tocopherol acetate, glycyrrhetic acid, nonylic vanylylamide, capsicum extract and the like), buffering agents, pH regulators, and the like.

In producing the external preparation of the present invention, it is preferable that etodolac or a salt thereof and a local anesthetic or a salt thereof are mixed first. Specifically, both compounds are added to a solvent and mixed with stirring, or both compounds are directly mixed while heating.

The salts used here are not particularly restricted as long as they are pharmaceutically acceptable. Even if the salts are used as an ingredient, the object of the present invention is thought to be achieved by strong interaction of the etodolac and the local anesthetic.

Examples of the salts of the local anesthetic which can be used as an active ingredient in the present invention include hydrohalogenates such as hydrofluoride, hydrochloride, hydrobromide, hydroiodide and the like; salts of inorganic acid such as nitrate, perchlorate, sulfate, phosphate and the like; salts of lower alkanesulfonic acids such as methanesulfonate, trifluoromethanesulfonate, ethanesulofnate and the like; salts of arylsulfonic acids such as benzenesulfonate, p-toluenesulfonate and the like; amino acid salts such as ornithinate and glutamate; and carboxylates such as fumarate, succinate, citrate, tartarate, oxalate, maleate and the like. Among them, hydrochloride can be used most suitably.

When the etodolac and the local anesthetic are mixed in a solvent, the solvents generally used in producing a medical composition are preferable. Since an oily matter is formed just by mixing etodolac and a local anesthetic with heating, preparation without solvent is also possible. For example, by putting both compounds in a mortar and grinding them while mixing, an oily matter can be formed with friction heat.

In the present invention, a local anesthetic can be used not only for reducing skin irritation but also as a solvent or solubilizing agent for the etodolac. Further, by allowing these local anesthetics to be contained, skin permeability, and penetratability and diffusivity of the etodolac are also improved, though the reason for this is not necessarily clear.

Compounding components corresponding to the dosage forms described above may be added and mixed into the resulting mixture of the etodolac and the local anesthetic. A known method corresponding to each dosage form may be adopted as the preparation method.

The anti-inflammatory analgesic for external use of the present invention thus obtained can achieve its effect sufficiently even if the etodolac is compounded in a larger amount as compared with conventional etodolac-containing external preparations. Since penetratability and diffusivity in deeper portions of the skin as well as skin permeability are improved, the drug does not accumulate on the surface portion of the skin. As the result, the drug has little skin irritation, and besides, it can be delivered to an affected area such as muscle tissue, joint tissue and the like. Therefore, the external preparation of the present invention is etodolac preparation which can be directly applied to an affected area of chronic pain and the like, and has an excellent effect.

The amount of use of the external preparation of the present invention varies depending on the kind of active ingredient, conditions and age of a patient, and the like, but generally, it is preferable that the external preparation is applied once to several times per day for an adult. More preferably, the external preparation is applied once to twice per day, and the administration frequency may be increased depending on conditions.

The present invention will be described in more detail by examples below, but the present invention is essentially not limited by the following examples, and appropriate alterations can be made on it to an extent applicable to the above-described and later-described points. All of them are included in the technological scope of the present invention.

EXAMPLES

Production Example 1

According to compounding ratios shown in Table 1, etodolac and so on were dissolved in Macrogol 400 to prepare sample solution 1 containing etodolac and lidocaine and sample solution 2 containing only etodolac. The numerical value in Table 1 is the ratio by mass.

TABLE 1

|  | Sample solution 1 | Sample solution 2 |
|---|---|---|
| Etodolac | 10 | 10 |
| Lidocaine | 10 | 0 |
| Macrogol 400 | 80 | 90 |

Test Example 1

Test of Penetratability and Diffusivity in Muscle Tissue

The penetratability and diffusivity into a meat piece of the etodolac-containing sample solutions 1 and 2 prepared in the above-described Production Example 1 were tested. First, gauze was spread on a petri dish having a diameter of 9 cm, and 10 g of the sample solution 1 or 2 was added. Separately, a lean beef was cut into cubes of 2×2×4 cm. The cut beef was placed on gauze so that a surface of 2×2 cm became the bottom, coated with a polyvinylidene chloride film, and allowed to stand still at 4° C. for 48 hours. Thereafter, the meat piece was cut every 1 cm from the bottom, and the concentration of etodolac was measured in terms of an amount contained in 1 g of meat piece, in the three fractions of 0 to 1 cm, 1 to 2 cm, and 2 to 3 cm from the bottom. For measuring the concentration, each meat piece was ground, and 5 mL of methanol was added to extract etodolac, and then the extract was analyzed by high performance liquid chromatography. The test was carried out 6 times for each sample solution. The results are shown in Table 2 as an average value. The fraction of 0 to 1 cm was excluded from the results since it was in direct contact with the sample solution.

TABLE 2

|  | Sample solution 1 | Sample solution 2 |
|---|---|---|
| 1 to 2 cm | 0.044 mg/mg | 0.006 mg/mg |
| 2 to 3 cm | 0.038 mg/mg | 0.007 mg/mg |

These results demonstrate that the penetratability and diffusivity of etodolac in muscle tissue is remarkably improved when lidocaine is compounded, and etodolac reaches the fraction of a depth of 2 to 3 cm. According to findings of the present inventors, the external preparation containing etodolac and a local anesthetic is excellent also in skin permeability. Therefore, it is thought that, in the external preparation of the present invention, etodolac absorbed transdermally penetrates and diffuses continuously into deeper portion of the skin without remaining on the surface portion of skin, and can act directly on an affected area.

Production Example 2

Preparation of Tape Preparation According to the Present Invention

According to compounding ratios by mass shown in Table 3, an etodolac-lidocaine compounded tape preparation was prepared by a solvent method with toluene. Specifically, first, etodolac, lidocaine and Macrogol were mixed with heating at 40° C. until the mixture became clear. Separately, styrene-isoprene-styrene block copolymer, liquid paraffin, alicyclic saturated hydrocarbon resin, and dibutylhydroxytoluene were dissolved in toluene, and to this mixture was added the mixture of etodolac and lidocaine to obtain a homogenously fused substance. With this fused substance, a releasing film consisting of polyester was coated using a coater so that the plaster weight after drying was 100 g/m². Then, the film as dried with heating to evaporate toluene. On the resulting coated surface, a supporting substrate consisting of non-woven fabric was pasted, and this was cut into a desired size to obtain a tape preparation.

TABLE 3

|  | Compounding ratio |
|---|---|
| Etodolac | 5 |
| Lidocaine | 4 |
| Diethyl sebacate | 2 |
| Styrene-isoprene-styrene block copolymer | 8 |
| Liquid paraffin | 20 |
| Alicyclic saturated hydrocarbon resin | 16 |
| Dibutylhydroxytoluene | 1 |
| Macrogol | 7 |
| Glycerin | 35 |
| Polybutene | 2 |

The invention claimed is:

1. An anti-inflammatory analgesic for external use comprising etodolac and lidocaine, wherein a molar ratio of the lidocaine to the etodolac is 1.

2. A plaster preparation comprising the anti-inflammatory analgesic according to claim 1.

* * * * *

UNITED STATES PATENT AND TRADEMARK OFFICE
CERTIFICATE OF CORRECTION

PATENT NO. : 7,655,687 B2
APPLICATION NO. : 10/587862
DATED : February 2, 2010
INVENTOR(S) : Hamamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 661 days.

Signed and Sealed this

Twenty-eighth Day of December, 2010

David J. Kappos
*Director of the United States Patent and Trademark Office*